US006189859B1

(12) United States Patent
Rohrbough et al.

(10) Patent No.: US 6,189,859 B1
(45) Date of Patent: Feb. 20, 2001

(54) INDWELLING CATHETER VALVE

(75) Inventors: John D. Rohrbough, Scottsdale, AZ (US); Michael D. Olichney, Lyons, CO (US)

(73) Assignee: Faulding Inc., Elizabeth, NJ (US)

( * ) Notice: Under 35 U.S.C. 154(b), the term of this patent shall be extended for 0 days.

(21) Appl. No.: 09/230,669

(22) PCT Filed: Jul. 30, 1997

(86) PCT No.: PCT/US97/13283

§ 371 Date: Sep. 23, 1999

§ 102(e) Date: Sep. 23, 1999

(87) PCT Pub. No.: WO98/05368

PCT Pub. Date: Feb. 12, 1998

(30) Foreign Application Priority Data

Aug. 1, 1996 (AU) ............................................. 1354

(51) Int. Cl.[7] .................................................. F16L 37/28
(52) U.S. Cl. ...................... 251/149.1; 604/256; 604/905
(58) Field of Search ........................ 251/149.1; 604/905, 604/256

(56) References Cited

U.S. PATENT DOCUMENTS

| 4,610,469 | 9/1986 | Wolff-Mooij | 285/260 |
|---|---|---|---|
| 4,895,565 | 1/1990 | Hillstead | 604/167 |
| 5,163,922 | 11/1992 | McElveen, Jr. et al. | 604/249 |
| 5,492,147 | * 2/1996 | Challender et al. | 251/149.1 |
| 5,549,577 | * 8/1996 | Siegel et al. | 604/256 |
| 5,699,821 | 12/1997 | Paradis | 137/1 |
| 5,806,831 | * 9/1998 | Paradis | 251/149.1 |
| 5,839,715 | * 11/1998 | Leinsing | 251/149.1 |
| 6,050,978 | * 4/2000 | Orr et al. | 604/249 |

* cited by examiner

Primary Examiner—A. Michael Chambers
(74) Attorney, Agent, or Firm—Christie, Parker & Hale, LLP

(57) ABSTRACT

A valve 1 suitable for use on an indwelling catheter is disclosed. Broadly the valve 1 comprises a valve housing 2 having an elongate valve insert 3 disposed therein. The housing 2 has an inlet 4 at one end thereof and an outlet 5 at an opposed end thereof and defines a longitudinal passage 7 extending from the inlet 4 to the outlet 5.

The valve insert 3 includes a cannula 25 having an inlet 26 towards one end 27 thereof and an outlet 28 towards an opposed end 29 thereof. The inlet end 27 of the cannula 25 terminates in a sharp point. The outlet end 29 by contrast is rounded and the actual outlet 28 is spaced axially inwardly from the end 29. The valve insert 3 further includes a seal 40 comprising an annular body 41 of resilient material defining an opening 42 therein through which the outlet end 29 of the cannula 25 projects. The seal 40 has an axial end surface which sealingly engages a seat 19 defined by the housing 2. The cannula 25 is displaceable in the housing 2 between a closed position in which the outlet 28 is upstream of the seal 40 and an open position in which the outlet 28 is downstream of the seal 40.

The valve insert 3 further includes biasing means in the form of a resilient sleeve 50 loaded under compression for urging the cannula 25 to the closed position. The compression loading in the sleeve 50 also urges the seal 40 into engagement with the seat 19. Typically the valve insert 3 also includes a further sleeve 60 for extending over and around the inlet of the cannula 25. In use the sleeve 60 is punctured by the sharp point on the end 27 of the cannula 25.

27 Claims, 5 Drawing Sheets

INDWELLING CATHETER VALVE

This invention relates to a valve. This invention relates particularly to a valve used in a catheter for administering fluid intravenously to a patient and for drawing body fluid from a patient. The invention also extends to a valve insert for use in the valve and a resilient element for use in the valve.

When medicament needs to be administered intravenously to a patient on a regular basis, it is a common medical procedure to insert an indwelling catheter into a blood vessel of a patient. This obviates the need to puncture the patient's skin each time medicament needs to be administered.

The indwelling catheter naturally includes a fitting or valve which stops the flow of blood out of a patient's blood vessel through the catheter while at the same time permitting intermittent access to the venous site for the purposes described above. Such fittings or valves are known in the art as intermittent caps.

Several known prior art intermittent caps suffer from the disadvantage that they have relatively large flow paths which are open to contamination and it is difficult to sterilise these flow paths each time medicament is administered.

Another known valve is disclosed in U.S. Pat. No. 5,065,783 granted to Ogle the entire contents of which are specifically incorporated herein by reference. Ogle discloses a valve housing having a cannula disposed therein and movable between open and closed positions. The cannula has opposed first and second sharp ends and first and second flexible elastomeric sleeves extending around respectively the first and second sharp ends. Each sleeve is attached to the cannula at a point intermediate the ends thereof and the closed end of the sleeve is free to move axially relative to the cannula. In the closed position each of the sleeves extend around respectively the first and second sharp ends of the cannula acting as a barrier to liquid flow therethrough. When a syringe nozzle is inserted into the valve housing, the first and second sleeves, are moved relative to the cannula to the open position where the sharp ends of the cannula pierce and penetrate the sleeves. This enables fluid to flow through the valve housing from the inlet to the outlet and also in a reverse direction from the outlet to the inlet.

However a shortcoming of this valve is that it only provides limited resistance to unwanted reverse or back flow through the valve when there is no syringe nozzle inserted in the valve housing. Fluid pressure in the reverse direction may force the sharp end of the cannula on the patient side ie proximate the outlet to pierce the adjacent sleeve and possibly open the cannula to fluid flow. It would obviously be advantageous if a valve could be provided which had substantially increased resistance to back or reverse flow.

In this specification the term cannula shall be given a broad meaning and shall be interpreted to include members of the same general type as the cannula described in the Ogle patent above. It shall not be limited to a tube fitted with a trocar for insertion into the body.

While it is convenient in this specification to refer to the inlet and outlet of the housing and the inlet and outlet of the cannula, it is to be clearly understood that the valve can be used to pass fluids therethrough in both directions. In essence the function of the valve is to provide a closure for the catheter flow path which flowpath can be opened as and when required by the insertion of a syringe nozzle into the housing. Such syringe can then be used to inject medicament into a patient or to withdraw a body fluid sample, eg blood sample from the patient. Injected medicament passes through the valve in a forward direction from inlet to outlet whereas a blood sample flows in a reverse direction through the valve.

It is an object of this invention to provide a valve which is suitable for use in an indwelling catheter and also which resists unwanted fluid flow in a reverse direction when subjected to back pressure.

According to a first aspect of this invention there is provided a valve housing having an inlet and an outlet and defining a passage from said inlet to said outlet;

an elongate cannula within the passage of the housing having an inlet towards one end thereof and an outlet towards an opposed end thereof, and defining a flow path from said inlet to said outlet;

a seal comprising a body defining an opening through which the outlet end of the cannula is passed, said body sealingly engaging each of the cannula and the housing, and said cannula being displaceable relative to said seal between a closed position in which the cannula outlet is upstream of said seal and an open position in which the cannula outlet is downstream of said seal placing the cannula outlet in fluid communication with the housing outlet; and biasing means biasing the cannula to the closed position.

Typically the body of the seal is of resilient material and said resilient material urges radially inwardly against the cannula which is passed through said opening in the seal.

Preferably the biasing means comprises a sleeve of resilient material extending around the cannula, one end of which is attached to an intermediate point on the cannula and the other end of which urges against the seal, said sleeve being loaded under compression in a longitudinal direction.

Advantageously said seal and said sleeve are formed by an integral body of resilient material, eg a single unitary body.

Further advantageously the outlet end of the cannula is rounded to ease its sliding displacement in the passage and said outlet is spaced axially inwardly of the outlet end of the cannula.

Typically said seal has one surface in sealing engagement with the cannula, and a further surface in sealing engagement with the housing.

Advantageously said one surface extends substantially in the longitudinal direction of the cannula and said further surface extends transversely to said one surface.

Typically said housing defines a seat extending transversely to the longitudinal axis of the housing and said further surface sealingly engages said seat.

Advantageously said seat includes a projection projecting outwardly proud of the remainder of the seat, to enhance the sealing of the seal to the housing.

In a preferred form said projection tapers inwardly in a direction axially outwardly away from the seat to a sharp point and said projection extends circumferentially around the cannula. In a preferred form the projection forms a substantially annular knife-edge seal.

Typically the valve includes a further sleeve of resilient material having a closed end and an opposed open end, said closed end extending circumferentially around the inlet end of the cannula and said open end being attached to a further intermediate point on the cannula.

Preferably the inlet end of the cannula is sharp to enable the end to penetrate the closed end of the further sleeve.

Advantageously said one and further sleeves are made of elastomeric material. Further advantageously each of said one and further sleeves has a plurality of circumferentially extending zones of increased thickness located at spaced intervals along the length of the sleeve.

Preferably the valve also includes means for guiding axial displacement of the cannula relative to the housing between said open and closed positions. Preferably said guide means includes at least one guide formation on the cannula received within a complementary internal guide formation defined by the housing.

In a preferred form said guide formation comprises a radially outwardly projecting flange-like formation disposed intermediate the ends of the cannula, and said complementary internal guide formation is defined by a complementary configuration of a longitudinal section of the passage of the housing.

Advantageously the housing further includes stop formations for defining respectively said open and closed positions of the cannula and for limiting movement of the cannula to movement between said open and closed positions. In a preferred form said stop formations engage the radially outwardly projecting flange-like formation to check displacement of the cannula.

According to another aspect of this invention there is provided a valve insert for a valve used in a catheter for administering fluid intravenously to a patient, including:

an elongate cannula having an inlet towards one end thereof and an outlet towards an opposed end thereof;

a seal comprising a body defining an opening through which the outlet end of the cannula is passed, said body sealingly engaging that portion of the cannula received in said opening and in use sealingly engaging an inner wall of a valve housing, the cannula being slideable relative to the body through which it is passed between a closed position in which the outlet is upstream of the body and an open position in which the outlet is downstream of the body; and a resilient sleeve having two opposed ends and extending circumferentially around the cannula in the longitudinal direction of the cannula, one said end being secured to an intermediate point on the cannula and the other said end engaging the body of the seal, the sleeve urging axially outwardly against the seal when loaded under compression.

The cannula, seal and sleeve may include any one or more of the preferred features described above with respect to the first aspect of the invention.

According to yet another aspect of this invention there is provided a resilient element for mounting over a cannula, including:

a hollow sleeve portion of resilient material having one open end which is in use is attached to an intermediate point on a cannula, and an opposed end which in use is slideable relative to the cannula; and a seal portion connected to said opposed end of said sleeve portion, said seal portion comprising a body of resilient material defining an opening therethrough, through which in use the cannula projects.

A valve in accordance with this invention may come in a variety of forms. It will be convenient to hereinafter describe in detail two specific embodiments of the invention with reference to the accompanying set of drawings. It is to be clearly understood however that the specific nature of this description does not supersede the generality of the preceding description. In the drawings.

Figure 1:
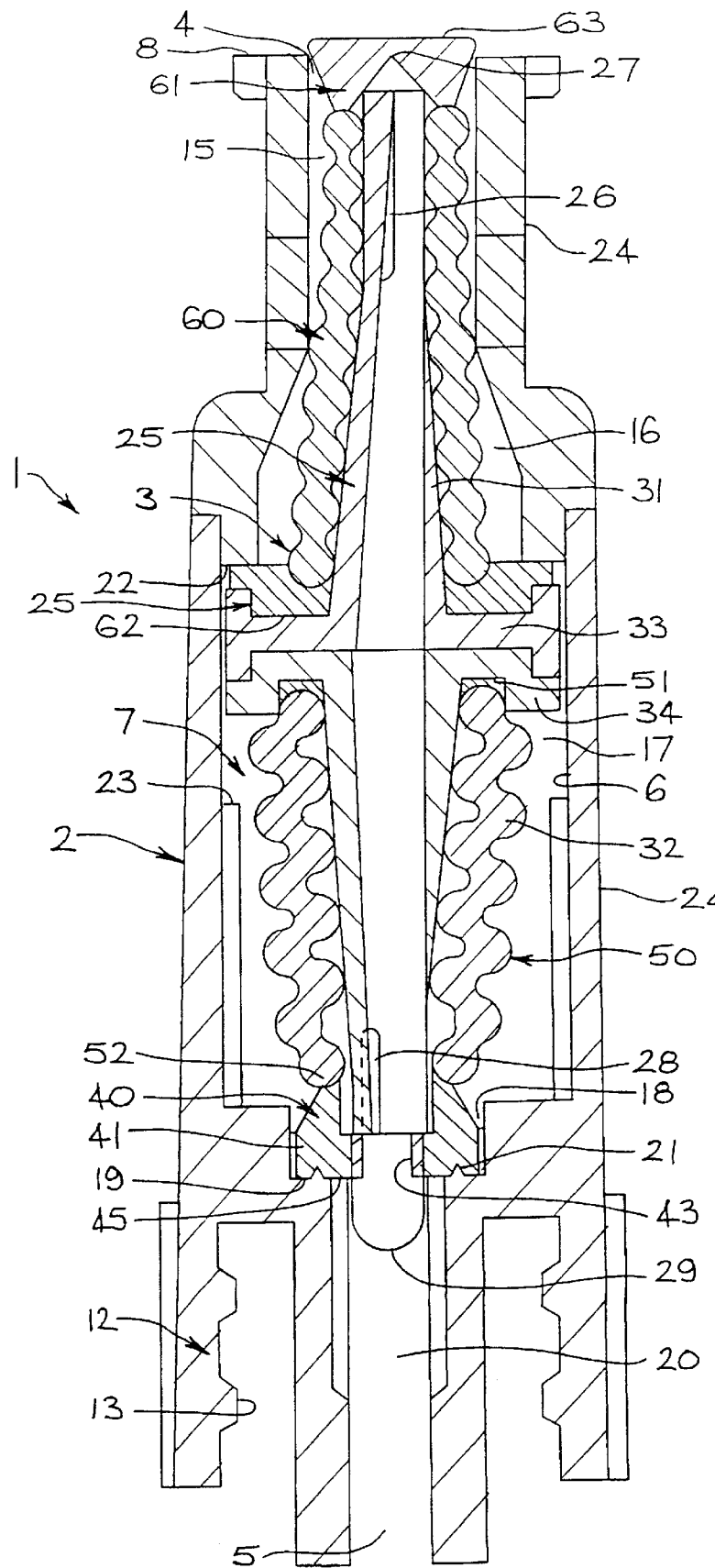
FIG. 1 is a sectional front elevation of a valve in accordance with one embodiment of the invention, in a closed position.
Figure 2:
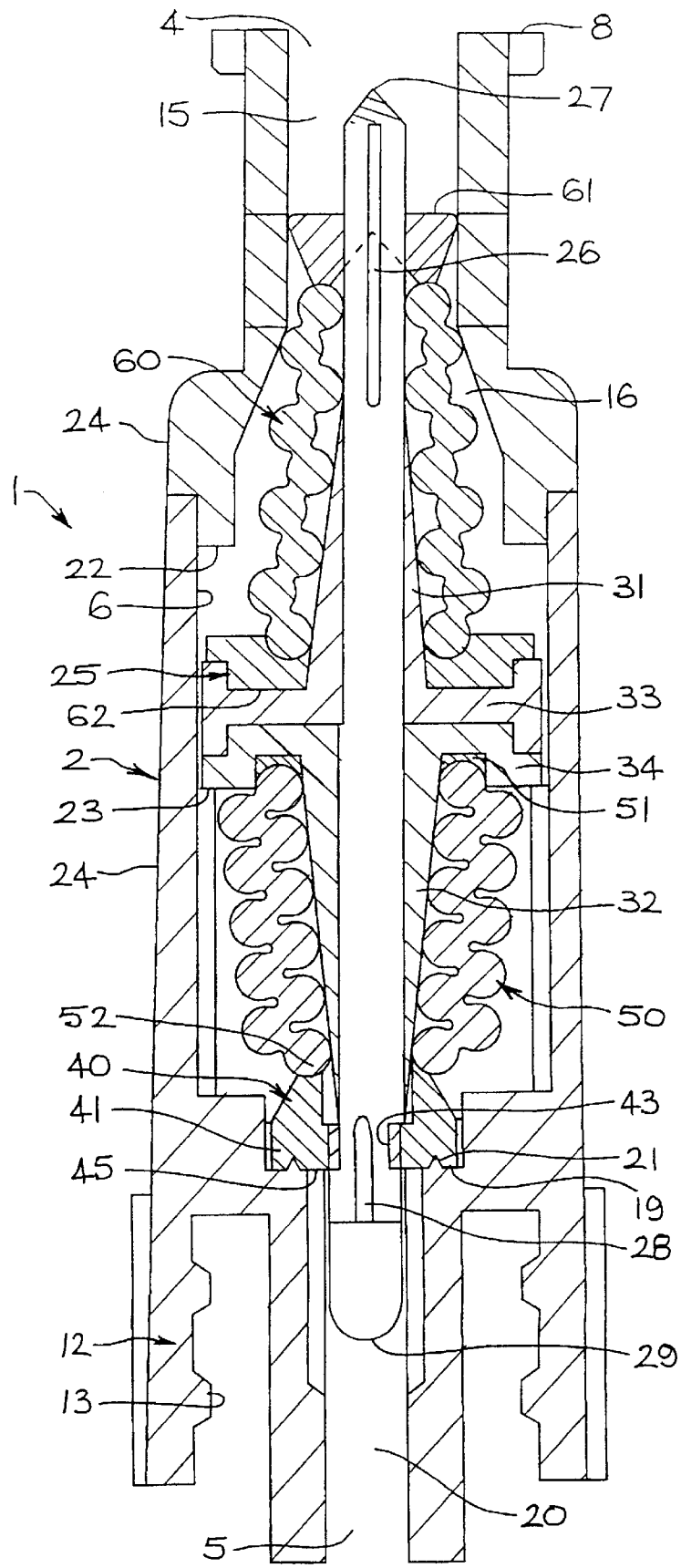
FIG. 2 is sectional front elevation of the valve of FIG. 1 in an open position.
Figure 3:
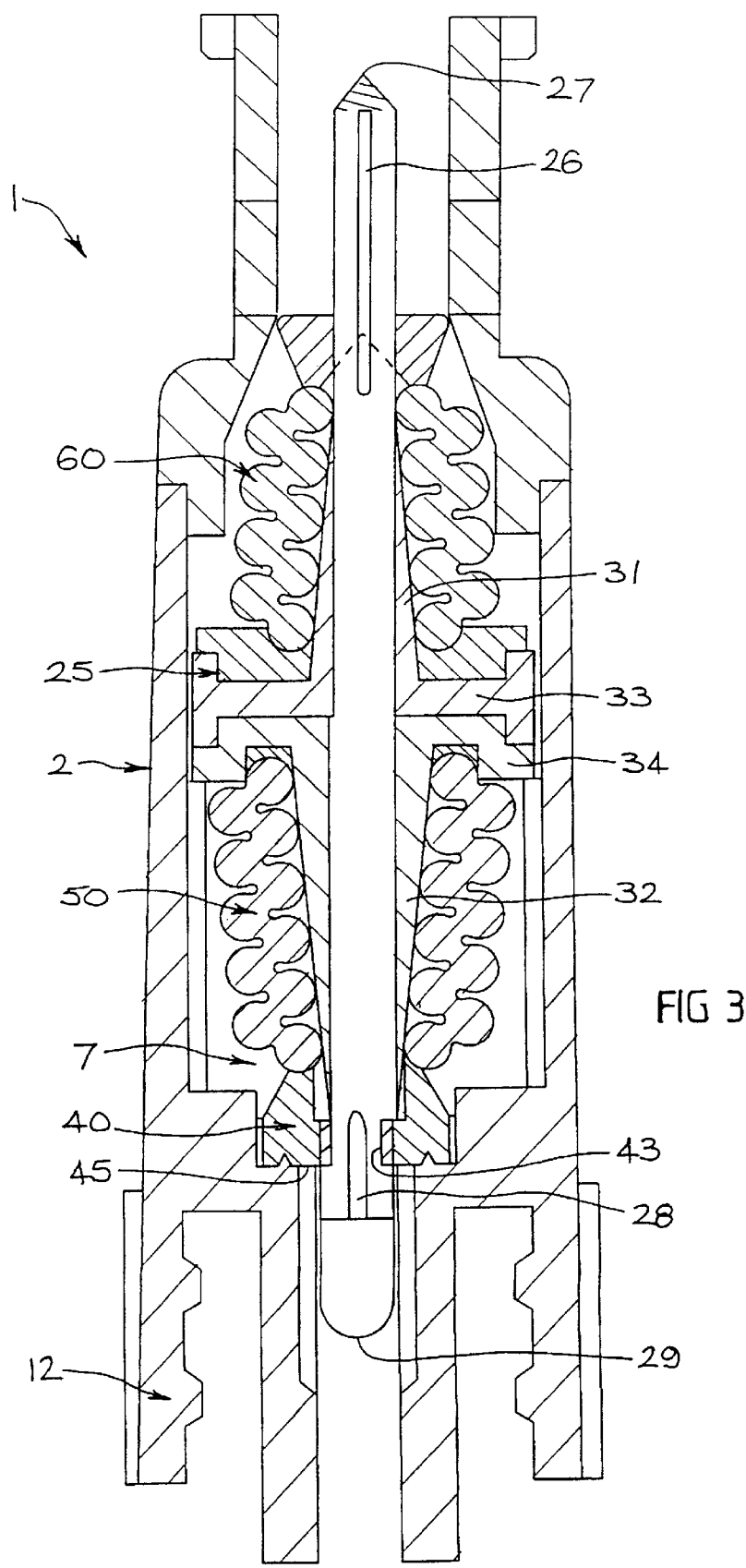
FIG. 3 is sectional front elevation of the valve of FIG. 1 also in an open position.

FIGS. 1 to 3 illustrate a valve in accordance with the invention indicated generally by reference numeral 1. The valve 1 comprises broadly a valve housing 2 and a valve insert 3 received within the housing 2.

The housing 2 is broadly circular cylindrical having an inlet 4 at one end thereof and an outlet 5 at the other end thereof. The housing also includes an internal wall 6 defining a longitudinal passageway or bore 7 extending from the inlet 4 through to the outlet 5.

The inlet 4 is typically circular cylindrical and is sized to receive the nozzle of a syringe therein with a small amount of clearance. A flange 8 extends radially outwardly away from the inlet 4 of the housing 2 to provide an abutment surface for the axial end surface of a hypodermic syringe.

The outlet 5 of the housing 2 is in the form of a Luer-lock collar 12. The collar 12 includes the usual internal threads 13 for mating with the external ears (not shown) on an indwelling catheter (not shown). Such Luer-lock collars 12 are well known to persons skilled in the art and will not be described in further detail here.

The longitudinal passageway 7 through the housing 2 includes a circular-cylindrical inlet portion 15 adjacent the inlet 4 which leads into an outwardly tapering conical portion 16 downstream of the inlet portion 15. A circular cylindrical central portion 17 is disposed about midway along the length of the passageway 7. A seal portion 18 having a seat 19 for receiving a seal (described in more detail below) is disposed downstream of the central portion 17. The seal portion 18 of the passageway 7 is of smaller diameter than the central portion 17. A circular cylindrical outlet portion 20 is disposed between the outlet 5 and the seal portion 18.

Figure 4:
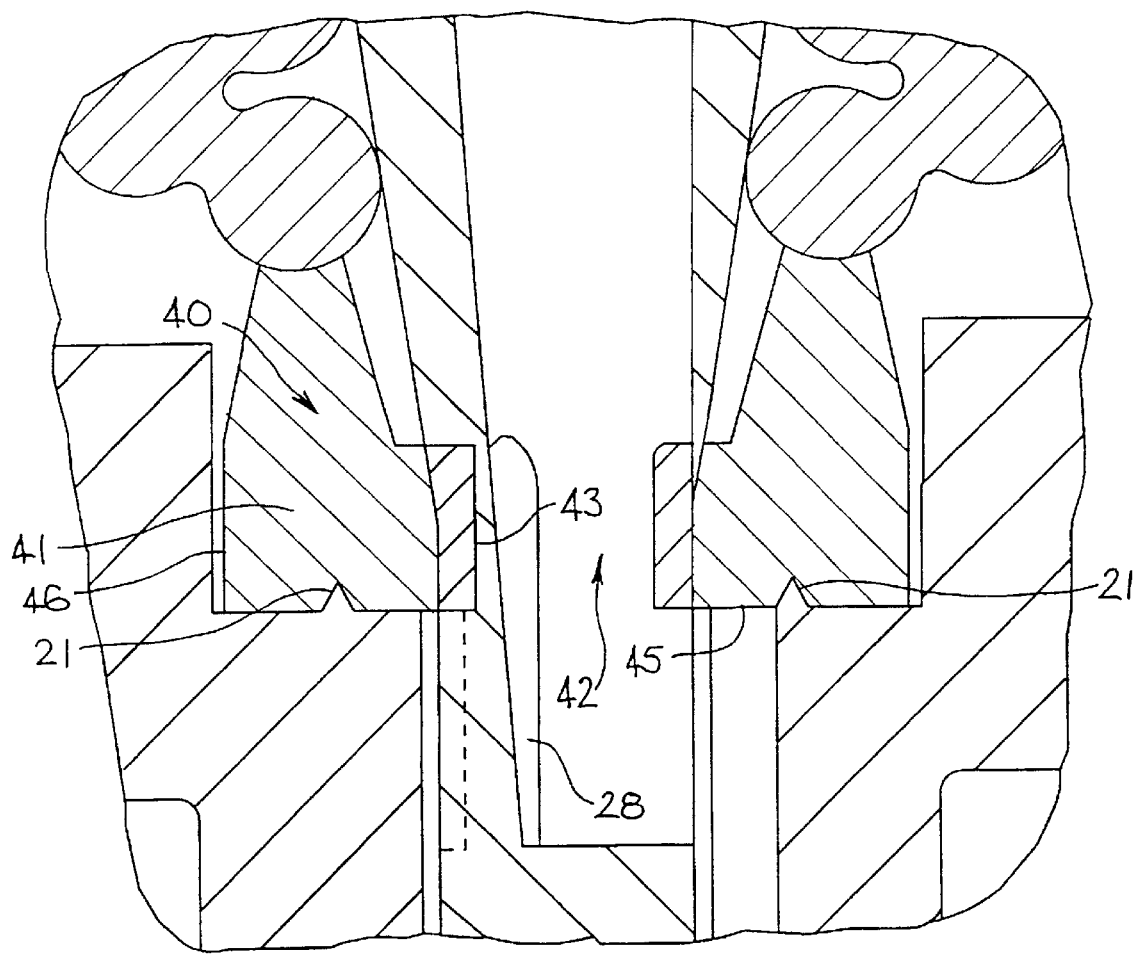
FIG. 4 is sectional front elevation of a portion of the valve showing the cross-sectional configuration of the knife edge sealing ring on the valve seat.
Figure 5:
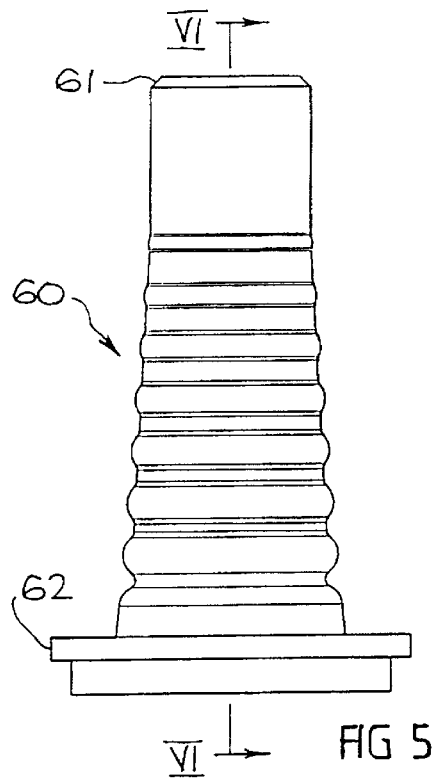
FIG. 5 is a front elevation of an inlet or syringe-side sleeve for a valve in accordance with a second embodiment of the invention.
Figure 6:
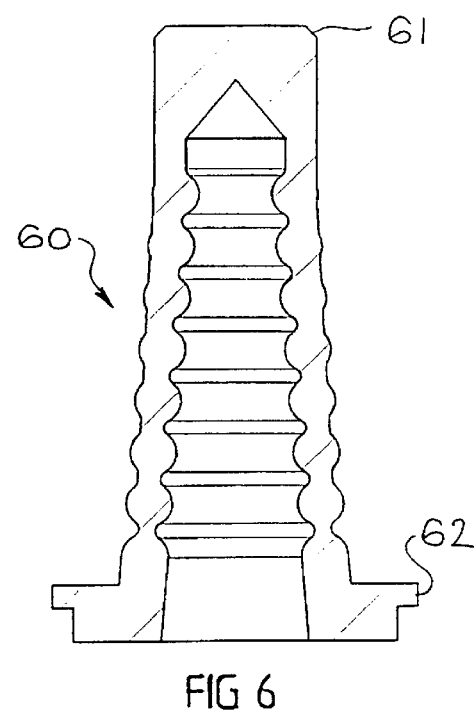
FIG. 6 is a sectional front elevation of the sleeve of FIG. 5.
Figure 7:
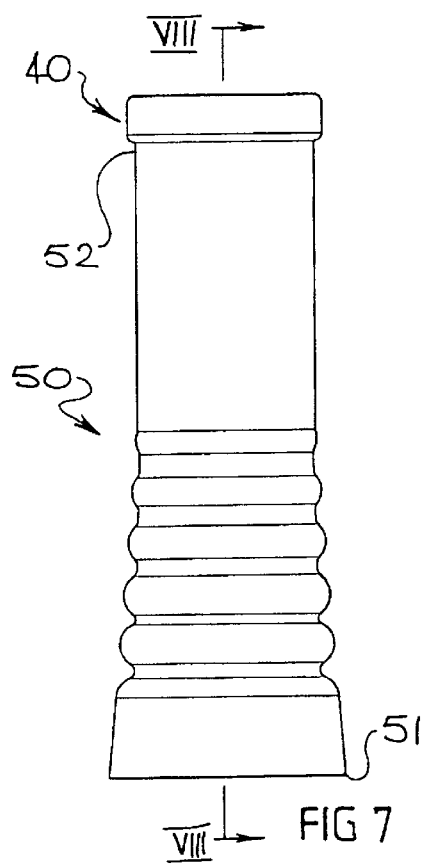
FIG. 7 is a front elevation of an outlet or patient-side sleeve for the valve in accordance with the second embodiment of the invention.
Figure 8:
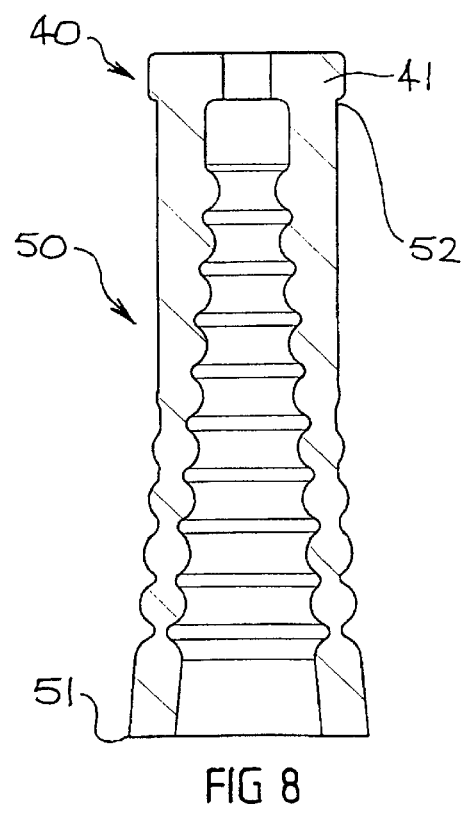
FIG. 8 is a sectional front elevation of the sleeve of FIG. 7.

Looking now specifically at the seat 19, an annular projection 21 projects upwardly proud of the remainder of the seat 19. This projection 21 has a triangular cross-section terminating in a sharp pointed knife edge which engages a seal on the cannula (described below). The knife edge has the effect of concentrating the pressure of the seal and produces a particular efficacious seal. The knife edge 21 is shown particularly clearly in FIG. 4.

Two axially spaced stop formations 22 and 23 define the limits of axial movement of the valve insert 3 within the housing 2. The stop formations 22 and 23 may be formed by shoulders extending radially inwardly into the passageway 7. It is to be appreciated however that the stop formations may take other forms.

Conveniently the housing may be assembled from two appropriately shaped housing portions 24 connected end-to-end although obviously this is not essential.

The valve insert 3 comprises a cannula 25 displaceable in the valve housing 2.

The cannula 25 has an inlet 26 at one end 27 thereof and an outlet 28 at the longitudinally opposed end 29 thereof.

The inlet end 27 of the cannula 25 has a sharp point whereas the outlet end 29 is rounded with the actual outlet 28 being spaced axially inward of the end 29. The cannula 25 is movable between a closed position in which fluid cannot flow from the cannula outlet 25 to the housing outlet 5 and an open position permitting fluid flow through the cannula outlet 28.

The cannula 25 is conveniently formed from two cannula portions 31 and 32 arranged end-to-end and attached to each other via attachment flanges 33 and 34 which are in face to face abutment.

The valve insert 2 further includes a seal 40 sealing the cannula 25 to the housing 2 to resist fluid flow in a reverse direction through the valve 1, ie from the outlet 5 to the inlet 4, when the cannula 25 is in the closed position.

The seal 40 comprises a body 41 of resilient material which has an annular opening 42 defined therein through which the outlet end 29 of the cannula 25 projects. The opening 42 in the seal 40 is defined by a cylindrical inner surface 43 which engages the cylindrical wall of the cannula 25. The opening 42 in the seal 40 is sized such that the body 41 of resilient material urges radially inwardly tightly over the cylindrical wall of the cannula 25 passing therethrough.

The seal 40 has an axial end surface 45, typically annular, which engages the seat 19 on the housing 2. The size and configuration of the end surface 45 is generally complementary to the seat 19, ie the seat 19 is arranged such that most of the end surface 45 is in contact with the seat 19. The circumferentially outer surface 46 of the seal 40 is received with a small amount of clearance within the seal portion 18 of the passageway 7.

The insert 2 also includes biasing means in the form of a resilient sleeve 50 mounted over the second cannula portion 32 biasing the cannula 25 to the closed position. The sleeve 50 has two open ends 51 and 52 and is made of elastomeric material. The open end 51 of the sleeve 50 is typically secured to the flange 34 of the cannula portion 32. In the illustrated embodiment the end 51 of the sleeve 50 is received within an annular channel defined in the flange 34, and secured to the channel, eg by adhesive. The sleeve 50 extends towards the outlet end of the cannula 25 with the end 52 of the sleeve 50 being positioned adjacent to the seal 40. The sleeve 50 is arranged such that it is loaded under compression even when the cannula 25 is in the closed position. The compression loading when the cannula 25 is in the closed portion is important because it urges the seal 40 into engagement with the seat 19.

In the illustrated embodiment the sleeve 50 and seal 40 are integral with each other having been formed as a single article in a single moulding operation. However it is to be clearly understood that this is not essential.

The valve insert 3 further includes a flexible elastomeric sleeve 60 having a closed end 61 and an open end 62 mounted over the first cannula portion 31. The closed end 61 of the sleeve 60 extends around the sharp tip of the end 27 of the cannula 25. The open end 62 of the sleeve 60 is secured to the flange 33 of the first cannula portion 31 in a similar manner to the attachment of the open end 51 of the sleeve 50 to the flange 34. The sleeve 60 is made of an elastomeric material that is easily penetrated by the sharp end 27 of the cannula 25. The closed end 61 of the sleeve 60 is shaped such that the portion 63 thereof which is in alignment with the sharp point of the cannula 25 has a reduced thickness.

Turning now to the spatial relationship between the various components of the valve insert 3 and the housing 2, the entrance and conical portions 15 and 16 of the passageway 7 are sized to receive the nozzle of a hypodermic syringe therein, and as a result the cannula 25 and sleeve 60 are received therein with generous clearance.

Guide means for guiding displacement of the cannula 25 in the housing 2 are provided by sizing the central portion 17 of the passageway 7 such that the flanges 33 and 34 have only a small clearance from the wall 6. This guides the cannula 25 axially in the passageway 7. The stop formations 22 and 23 located within the central portion 17 of the passageway 7 are arranged to engage the flanges 33 and 34 either directly or indirectly to define the extent of axial movement of the cannula 25 between the open and closed positions.

The outlet portion 20 of the passageway 7 is slightly larger than the diameter of the outlet end of the cannula 25 which is slidably received therein. The small clearance between the outlet end of the cannula 25 and the outlet portion of the passageway 7 assists in guiding displacement of the cannula 25 within the passageway 7. The outlet portion 20 is naturally configured to permit fluid to pass from the outlet 28 of the cannula 25 to the outlet 5 of the housing when the outlet 28 is downstream of the seal 40.

In use the valve 1 forms part of an indwelling catheter (not shown) which has been inserted into the blood vessel of a patient. The valve 1 is secured to the remainder of the catheter by means of the Luer-lock collar 12 which as described above is a fairly common fitting in medical devices of this nature.

FIG. 1 illustrates the valve 1 prior to it being engaged by a syringe for the purposes of either injecting medicament into a patient or withdrawing body fluid from the patient. The cannula 25 is in the closed position with the outlet 28 thereof being positioned upstream of the seal 40. The flange 33 either directly or indirectly through an attachment portion of the sleeve 60 engages the stop formation 22 in the closed position. In the FIG. 1 position, the sleeve 50 is axially loaded under compression to urge the end surface 45 of the seal 40 firmly into engagement with the seat 19.

The seal 40 resists flow between the cannula 25 and the body 41 and between the body 41 and the inner wall 6 of the housing 2. Fluid pressure in a reverse direction from the housing outlet side 5 or patient side would tend to urge the cannula 25 axially inwardly. However because of the structural features of the valve this would not tend to place the cannula outlet 28 in fluid communication with the housing outlet 5. Further the seal 40 is largely shielded against fluid pressure in a reverse direction by the seat 19 and would not be easily lifted off the seat 19 by this pressure. Thus the valve is not prone to opening or permitting fluid flow in a reverse direction when exposed to back pressure. This is an important feature which distinguishes this valve over other known valves.

FIG. 2 illustrates the valve I when the nozzle of a hypodermic syringe (not shown) has been inserted through the housing inlet 4 into the inlet portion 15 of the passageway 7. The cannula 25 is moved axially within the passageway 7 by this inward movement of the nozzle of the syringe up to the point where it is in the open position with the outlet 28 being positioned downstream of the seal 40. This permits fluid to flow from the cannula 25 through the outlet 5 of the housing 2 and vice versa.

FIG. 3 shows the valve 1 when the syringe nozzle is fully inserted into the valve inlet portion 15. In the FIG. 3 position, the sleeve 60 has been displaced axially inwardly over the end 27 of the cannula 25 placing the housing inlet 4 and cannula inlet 27 in fluid communication and fully opening the valve 1 to fluid flow therethrough. Both sleeves 50 and 60 are loaded under compression in the FIG. 3 position and the pressure applied by the nozzle of the syringe holds the cannula 25 in the open position.

When the syringe nozzle is withdrawn the components of the insert 3 return to the positions indicated in FIG. 1. The compression energy in the sleeve 50 moves the cannula 25 back to the closed position, ie such that the outlet 28 is upstream of the seal 40. The compression energy in the sleeve 60 moves the sleeve 60 back over the sharp inlet end 27 of the cannula 25 such that it closes off the inlet 26.

FIGS. 5 to 8 illustrate alternative configurations for the seal 40 and sleeve 50, and the sleeve 60. The seal 40 and sleeve 50 is a single integral article as is the seal and sleeve in FIGS. 1 to 3. The seal 40 and sleeve 50 performs the same function as the sleeve and seal in the embodiment illustrated in FIGS. 1 to 3. Similarly the sleeve 60 in FIGS. 5 to 8 performs the same function as the sleeve 60 in FIGS. 1 to 3.

It is an advantage of the valve described above that it is highly resistant to back flow through the housing 2 from the outlet 5 to the inlet 4. The seal and the housing are designed so that such back pressure will not have the effect of tending to open the valve to fluid flow. For example the seat 19 is shielded from the pressure of the liquid and liquid pressure on the outlet end of the cannula 25 urges the cannula 25 in a direction opposite to the direction which would open the valve.

A further advantage of the valve described above and illustrated in FIGS. 1 to 3 is that it provides reliable and trouble-free operation which is important for medical devices. Further it can be produced relatively simply at reasonable cost.

It is to be understood that various alterations, modifications, and/or additions may be introduced into the construction and arrangement of the components previously described without departing from the ambit of the invention disclosed herein.

What is claimed is:

1. A valve including:
   a valve housing having an inlet and an outlet and defining a passage from the inlet to the outlet;
   an elongate cannula within the passage of the housing, the cannula having an inlet at one end thereof and an outlet adjacent and spaced from an opposed closed end thereof to define a flow path from the inlet to the outlet of the housing;
   a seal comprising a body defining an opening into which the closed outlet end of the cannula extends, the body making a sliding seal against the cannula in the vicinity of the cannula outlet, and a fixed seal against the housing, the cannula being displaceable relative to the seal body between a closed position in which the cannula outlet is upstream of the sliding seal and an open position in which the cannula outlet is downstream of the sliding seal thereby placing the cannula outlet in fluid communication with the housing outlet; and
   a spring urging the seal body to the closed position around the cannula outlet and against the housing at the fixed seal.

2. A valve according to claim 1, wherein the body of the seal is of resilient material and said resilient material urges radially inwardly against the cannula which is passed through said opening in the seal.

3. A valve according to any one of claims 1, 2, wherein the outlet end of the cannula is rounded to ease its sliding displacement in the passage.

4. A valve according to claim 1 or claim 2, wherein the spring is an impermeable sleeve of resilient material disposed around the cannula and extending in a longitudinal direction, one end of the sleeve being attached to an intermediate point on the cannula and the other end of the sleeve being against the seal, the sleeve being loaded under compression in a longitudinal direction in the closed position to urge the seal body against the housing at the fixed seal.

5. A valve according to claim 4, wherein said seal and said sleeve are an integral body of resilient material.

6. A valve according to claim 4, including a further sleeve of resilient material having a closed end which extends circumferentially around the inlet end of the cannula and an opposed open end, said open end being attached to a further intermediate point on the cannula.

7. A valve according to claim 6, wherein the inlet end of the cannula is sharp to enable the end to penetrate the closed end of the further sleeve.

8. A valve according to claim 6, wherein said one and further sleeves are made of elastomeric material.

9. A valve according to claim 8, wherein each of said one and further sleeves has a plurality of circumferentially extending zones of increased thickness located at spaced intervals along the length of the sleeve.

10. A valve according to claim 9, including means for guiding axial displacement of the cannula relative to the housing between said open and closed positions.

11. A valve according to claim 10, wherein said guide means includes at least one guide formation on the cannula received within a complementary internal guide formation defined by the housing.

12. A valve according to claim 11, wherein said guide formation comprises a radially outwardly projecting flange-like formation disposed intermediate the ends of the cannula, and said complementary internal guide formation is defined by a longitudinal section of the passage of the housing.

13. A valve according to claim 12, wherein the housing further includes stop formations for defining respectively said open and closed positions of the cannula and for limiting movement of the cannula to movement between said open and closed positions.

14. A valve according to claim 13, wherein said stop formations engage said radially outwardly projecting flange-like formation to check displacement of the cannula.

15. A valve according to claim 1, 2 or 5 wherein said housing defines a seat extending transversely to the longitudinal axis of the housing, and wherein the body sealingly engages said seat at the fixed seal.

16. A valve according to claim 15, wherein said seat includes a projection projecting away from the remainder of the seat, to enhance the sealing of the seal to the housing.

17. A valve according to claim 16, wherein said projection tapers inwardly in a direction axially outwardly away from the seat to a sharp point which extends circumferentially around the cannula.

18. A valve according to claim 17, wherein said projection forms a substantially annular knife-edge seal.

19. A resilient element for mounting over a cannula, including:
   a hollow sleeve portion of resilient material having one open end which in use is attached to an intermediate point on a cannula, and an opposed end which in use is slideable relative to the cannula; and
   a seal portion connected to said opposed end of said sleeve portion, said seal portion comprising a body of resilient material defining an opening therethrough, through which in use the cannula projects, the opening defined in the body of the seal being substantially annular with a longitudinal section sized such that in use the body is urged radially inwardly against the cannula, and with an annular transverse section sized such that in use the body is urged axially against a seat in a housing in which the cannula is disposed.

20. A resilient element according to claim 19, wherein the body of the seal has an end surface extending substantially perpendicular to the longitudinal axis of the sleeve portion.

21. A resilient element according to any one of claims 19 or 20, wherein the sleeve portion is formed integral with the seal portion.

22. A valve insert for a valve used in a catheter for administering fluid intravenously to a patient, including:

an elongate cannula having an inlet towards one end thereof and an outlet towards a closed opposed end thereof, the cannula outlet being adjacent and spaced from the closed end;

a seal comprising a body defining an opening through which the outlet end of the cannula extends, said body sealingly engaging that portion of the cannula received in said opening and in use sealingly engaging an inner wall of a valve housing, the cannula being slideable relative to the body through which it is passed between a closed position in which the outlet is downstream of the body and an open position in which the outlet is downstream of the body; and a resilient sleeve having two opposed ends and extending circumferentially around the cannula in the longitudinal direction of the cannula, one said end being secured to an intermediate point on the cannula and the other said end engaging the body of the seal, the sleeve urging axially outwardly against the seal when loaded under compression.

23. A valve insert according to claim 22, wherein the body of the seal is made of resilient material.

24. A valve insert according to claim 23, wherein the body of the seal and the sleeve are in the form of an integral article made of elastomeric material.

25. A valve insert according to any one of claims 22 to 24, wherein said seal has one surface in sealing engagement with the cannula and a further surface in sealing engagement with the housing.

26. A valve insert according to claim 25, wherein said one surface extends substantially in the longitudinal direction of the cannula, and said further surface extends transversely to said one surface.

27. A valve insert according to any one of claims 23,24 or any one of claims 22 to 26, including a further sleeve of resilient flexible material having one open end and one closed end, the open end being attached to a further intermediate point on the cannula, and the closed end thereof passing around the inlet end of the cannula.

* * * * *